United States Patent
Li

(10) Patent No.: US 9,907,484 B2
(45) Date of Patent: *Mar. 6, 2018

(54) ENDOBRONCHIAL TUBE APPARATUS

(71) Applicant: Medtronic Xomed, Inc., Jacksonville, FL (US)

(72) Inventor: Wenjeng Li, Saint Johns, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/219,726

(22) Filed: Jul. 26, 2016

(65) Prior Publication Data

US 2016/0345905 A1 Dec. 1, 2016

Related U.S. Application Data

(63) Continuation of application No. 14/747,257, filed on Jun. 23, 2015, now Pat. No. 9,398,865, which is a
(Continued)

(51) Int. Cl.
*A61B 5/0492* (2006.01)
*A61B 5/00* (2006.01)
(Continued)

(52) U.S. Cl.
CPC ........ *A61B 5/0492* (2013.01); *A61B 5/04886* (2013.01); *A61B 5/687* (2013.01);
(Continued)

(58) Field of Classification Search
CPC . A61B 5/0492; A61B 5/04886; A61B 5/6853; A61B 5/687
See application file for complete search history.

(56) References Cited

U.S. PATENT DOCUMENTS

| 1,864,688 A | 6/1932 | Frank |
| 2,107,835 A | 2/1938 | Pierce |

(Continued)

FOREIGN PATENT DOCUMENTS

| CN | 2056003 U | 4/1990 |
| CN | 2232257 Y | 8/1996 |

(Continued)

OTHER PUBLICATIONS

Australian Examination Report dated Feb. 25, 2013 (4 pages) re AU 2010300373.

(Continued)

*Primary Examiner* — Lee S Cohen
(74) *Attorney, Agent, or Firm* — Jeffrey J. Hohenshell

(57) ABSTRACT

Concepts presented herein include an apparatus for monitoring EMG signals of a patient's laryngeal muscles. The apparatus includes an endobronchial tube having an exterior surface and two lumens for providing ventilation. Conductive ink electrodes are formed on the exterior surface of the endobronchial tube. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

18 Claims, 3 Drawing Sheets

Related U.S. Application Data continuation of application No. 13/688,818, filed on Nov. 29, 2012, now Pat. No. 9,060,744.

(51) Int. Cl.
  *A61M 16/04* (2006.01)
  *A61B 5/0488* (2006.01)
  *A61M 16/08* (2006.01)

(52) U.S. Cl.
  CPC .......... *A61B 5/6847* (2013.01); *A61B 5/6853* (2013.01); *A61B 5/74* (2013.01); *A61M 16/0404* (2014.02); *A61M 16/0434* (2013.01); *A61M 16/0459* (2014.02); *A61M 16/0463* (2013.01); *A61M 16/0475* (2014.02); *A61M 16/0486* (2014.02); *A61M 16/0488* (2013.01); *A61M 16/0833* (2014.02); *A61M 16/0443* (2014.02); *A61M 2230/60* (2013.01)

(56) References Cited

U.S. PATENT DOCUMENTS

| | | | |
|---|---|---|---|
| 2,429,585 | A | 10/1947 | Rogoff |
| 2,618,684 | A | 11/1952 | Bergan |
| 2,872,505 | A | 2/1959 | Ustin |
| 3,165,575 | A | 1/1965 | Lynch, Jr. et al. |
| 3,494,364 | A | 2/1970 | Peters |
| 3,734,094 | A | 5/1973 | Calinog |
| 3,783,178 | A | 1/1974 | Philibert et al. |
| 3,892,455 | A | 7/1975 | Sotolongo |
| 3,951,136 | A | 4/1976 | Wall |
| 4,090,518 | A | 5/1978 | Elam |
| 4,176,660 | A | 12/1979 | Mylrea et al. |
| 4,231,365 | A | 11/1980 | Scarberry |
| 4,304,239 | A | 12/1981 | Perlin |
| 4,349,031 | A | 9/1982 | Perlin |
| 4,369,794 | A | 1/1983 | Furler |
| 4,647,713 | A | 3/1987 | de Nijs et al. |
| 4,776,808 | A | 10/1988 | Davidson |
| 4,836,214 | A | 6/1989 | Sramek |
| 4,863,390 | A | 9/1989 | Cera et al. |
| 4,890,623 | A | 1/1990 | Cook et al. |
| 4,906,244 | A | 3/1990 | Pinchuk et al. |
| 4,960,133 | A | 10/1990 | Hewson |
| 4,967,759 | A | 11/1990 | Teves |
| 5,024,228 | A | 6/1991 | Goldstone et al. |
| 5,096,445 | A | 3/1992 | Lostumo |
| 5,125,406 | A | 6/1992 | Goldstone et al. |
| 5,135,001 | A | 8/1992 | Sinofsky et al. |
| 5,170,803 | A | 12/1992 | Hewson et al. |
| 5,286,211 | A | 2/1994 | McIntosh |
| 5,364,281 | A | 11/1994 | Leto |
| 5,379,765 | A | 1/1995 | Kajiwara et al. |
| 5,429,617 | A | 7/1995 | Hammersmark et al. |
| 5,464,404 | A | 11/1995 | Abela et al. |
| 5,554,176 | A | 9/1996 | Maddison et al. |
| 5,584,290 | A | 12/1996 | Brain |
| 5,672,065 | A | 9/1997 | Womack |
| 5,782,744 | A | 7/1998 | Money |
| 5,782,774 | A | 7/1998 | Shmulewitz |
| 5,785,051 | A | 7/1998 | Lipscher et al. |
| 5,836,874 | A | 11/1998 | Swanson et al. |
| 5,864,093 | A | 1/1999 | Hecock et al. |
| 5,924,984 | A | 7/1999 | Rao |
| 5,972,026 | A | 10/1999 | Laufer et al. |
| 6,010,500 | A | 1/2000 | Sherman et al. |
| 6,032,065 | A | 2/2000 | Brown |
| 6,062,223 | A | 5/2000 | Palazzo et al. |
| 6,095,987 | A | 8/2000 | Shmulewitz et al. |
| 6,142,993 | A | 11/2000 | Whayne et al. |
| 6,148,222 | A | 11/2000 | Ramsey, III |
| 6,226,548 | B1 | 5/2001 | Foley et al. |
| 6,259,938 | B1 | 7/2001 | Zarychta et al. |
| 6,266,548 | B1 | 7/2001 | Lamade et al. |
| 6,266,549 | B1 | 7/2001 | Melnikoff et al. |
| 6,292,701 | B1 | 9/2001 | Prass et al. |
| 6,334,068 | B1 | 12/2001 | Hacker |
| 6,343,233 | B1 | 1/2002 | Werner et al. |
| 6,357,447 | B1 | 3/2002 | Swanson et al. |
| 6,443,156 | B1 | 9/2002 | Niklason et al. |
| 6,547,788 | B1 | 4/2003 | Maguire et al. |
| 6,584,347 | B1 | 6/2003 | Sinderby |
| 6,626,841 | B1 | 9/2003 | Atlee, III |
| 6,626,899 | B2 | 9/2003 | Houser et al. |
| 6,735,471 | B2 | 5/2004 | Hill et al. |
| 6,869,431 | B2 | 3/2005 | Maguire et al. |
| 6,877,512 | B2 | 4/2005 | Imai et al. |
| 6,976,857 | B1 | 12/2005 | Shukla et al. |
| 7,008,419 | B2 | 3/2006 | Shadduck |
| 7,146,222 | B2 | 12/2006 | Boling |
| 7,153,146 | B2 | 12/2006 | Shimizu et al. |
| 7,179,345 | B2 | 2/2007 | Shkolnik |
| 7,216,001 | B2 | 5/2007 | Hacker et al. |
| 7,293,562 | B2 | 11/2007 | Malecki et al. |
| 7,507,239 | B2 | 3/2009 | Shadduck |
| 7,583,991 | B2 | 9/2009 | Rea |
| 7,736,362 | B2 | 6/2010 | Eberl et al. |
| 7,794,256 | B1 | 9/2010 | Sochor |
| 7,972,308 | B2 | 7/2011 | Putz |
| 8,145,289 | B2 | 3/2012 | Calabro' et al. |
| 8,152,803 | B2 | 4/2012 | Edwards et al. |
| 8,224,422 | B2 | 7/2012 | Mottola et al. |
| 8,352,012 | B2 | 1/2013 | Besio |
| 8,467,844 | B2 | 6/2013 | Rea et al. |
| 8,634,894 | B2 | 1/2014 | Rea et al. |
| 8,688,237 | B2 | 4/2014 | Stanislaus et al. |
| 8,886,280 | B2 | 11/2014 | Kartush |
| 9,037,226 | B2 | 5/2015 | Hacker et al. |
| 9,060,744 | B2 | 6/2015 | Li |
| 9,289,141 | B2 | 3/2016 | Lowery et al. |
| 9,398,865 | B2 | 7/2016 | Li |
| 9,763,624 | B2 | 9/2017 | Stanislaus et al. |
| 2001/0018281 | A1 | 8/2001 | Royer |
| 2002/0016615 | A1 | 2/2002 | Dev et al. |
| 2002/0032468 | A1 | 3/2002 | Hill et al. |
| 2002/0188332 | A1 | 12/2002 | Lurie et al. |
| 2003/0018327 | A1 | 1/2003 | Truckai et al. |
| 2003/0074039 | A1 | 4/2003 | Puskas |
| 2004/0186461 | A1 | 9/2004 | DiMatteo |
| 2004/0230110 | A1 | 11/2004 | Sinderby et al. |
| 2005/0085111 | A1 | 4/2005 | Clark et al. |
| 2005/0113686 | A1 | 5/2005 | Peckham |
| 2005/0159659 | A1 | 7/2005 | Sawan et al. |
| 2005/0222656 | A1 | 10/2005 | Wahlstrand et al. |
| 2005/0255727 | A1 | 11/2005 | Alladice |
| 2006/0012671 | A1 | 1/2006 | Nimri et al. |
| 2006/0025702 | A1 | 2/2006 | Sterrantino et al. |
| 2006/0116564 | A1 | 6/2006 | Mintchev et al. |
| 2006/0241725 | A1 | 10/2006 | Libbus et al. |
| 2006/0254595 | A1 | 11/2006 | Rea |
| 2007/0074728 | A1 | 4/2007 | Rea |
| 2007/0137651 | A1 | 6/2007 | Glassenberg et al. |
| 2007/0142888 | A1 | 6/2007 | Chavez |
| 2007/0156041 | A1 | 7/2007 | Rea |
| 2007/0170928 | A1 | 7/2007 | Fedan et al. |
| 2007/0219551 | A1 | 9/2007 | Honour et al. |
| 2008/0077043 | A1 | 3/2008 | Malbrain et al. |
| 2008/0140052 | A1 | 6/2008 | Moller et al. |
| 2008/0177190 | A1 | 7/2008 | Libbus et al. |
| 2008/0249507 | A1 | 10/2008 | Hadani |
| 2008/0255441 | A1 | 10/2008 | Hadani |
| 2008/0300650 | A1 | 12/2008 | Gerber et al. |
| 2009/0227885 | A1 | 9/2009 | Lowery et al. |
| 2010/0006103 | A1 | 1/2010 | McGinnis et al. |
| 2010/0036229 | A1 | 2/2010 | Weekamp et al. |
| 2010/0063376 | A1 | 3/2010 | Kartush |
| 2010/0087782 | A1 | 4/2010 | Ghaffari et al. |
| 2010/0145178 | A1 | 6/2010 | Kartush |
| 2010/0168561 | A1 | 7/2010 | Anderson |
| 2010/0168743 | A1 | 7/2010 | Stone et al. |
| 2010/0179417 | A1 | 7/2010 | Russo |
| 2010/0191311 | A1 | 7/2010 | Scheiner et al. |
| 2010/0198099 | A1 | 8/2010 | Murphy et al. |
| 2010/0317956 | A1 | 12/2010 | Kartush |

(56) References Cited

U.S. PATENT DOCUMENTS

| | | |
|---|---|---|
| 2011/0023889 A1 | 2/2011 | Lin et al. |
| 2011/0030694 A1 | 2/2011 | Schaner et al. |
| 2011/0071379 A1 | 3/2011 | Rea et al. |
| 2011/0190596 A1 | 8/2011 | Hacker et al. |
| 2011/0230734 A1 | 9/2011 | Fain et al. |
| 2011/0245647 A1 | 10/2011 | Stanislaus et al. |
| 2011/0301587 A1 | 12/2011 | Deem et al. |
| 2011/0306861 A1 | 12/2011 | Thramann et al. |
| 2012/0016256 A1 | 1/2012 | Mabary et al. |
| 2012/0024292 A1 | 2/2012 | Sandmore et al. |
| 2012/0055257 A1 | 3/2012 | Shaw-Klein |
| 2013/0172714 A1 | 7/2013 | Li et al. |
| 2014/0148672 A1 | 5/2014 | Li |
| 2014/0155720 A1 | 6/2014 | Stanislaus et al. |
| 2014/0275914 A1 | 9/2014 | Li et al. |
| 2015/0250423 A1 | 9/2015 | Hacker et al. |
| 2016/0038072 A1 | 2/2016 | Brown et al. |
| 2016/0038073 A1 | 2/2016 | Brown et al. |
| 2016/0038074 A1 | 2/2016 | Brown et al. |
| 2016/0262699 A1 | 9/2016 | Goldstone et al. |
| 2016/0287112 A1 | 10/2016 | McFarlin et al. |
| 2016/0287861 A1 | 10/2016 | McFarlin et al. |
| 2016/0324475 A1 | 11/2016 | Hacker |
| 2017/0007146 A1 | 1/2017 | Schulhauser et al. |

FOREIGN PATENT DOCUMENTS

| | | |
|---|---|---|
| CN | 2827273 Y | 10/2006 |
| DE | 29715344 U1 | 2/1998 |
| DE | 19750705 C1 | 3/2000 |
| EP | 0438863 A1 | 7/1991 |
| EP | 1750368 A1 | 2/2007 |
| GB | 1214718 | 12/1970 |
| JP | H03182230 | 8/1991 |
| JP | 2001224554 A | 8/2001 |
| JP | 2003019200 A | 1/2003 |
| JP | 2003527164 A | 9/2003 |
| JP | 2006528890 A | 12/2006 |
| JP | 2007307185 A | 11/2007 |
| JP | 2007532152 A | 11/2007 |
| JP | 2009519763 A | 5/2009 |
| JP | 2009524482 A | 7/2009 |
| WO | 9723163 A1 | 7/1997 |
| WO | 0141638 A1 | 6/2001 |
| WO | 2004100786 A1 | 11/2004 |
| WO | 2005097246 A1 | 10/2005 |
| WO | 2006012671 A1 | 2/2006 |
| WO | 2006012672 A1 | 2/2006 |
| WO | 2007089491 A2 | 8/2007 |
| WO | 2007078827 A2 | 12/2007 |
| WO | 2008091928 A2 | 7/2008 |
| WO | 2011041690 A1 | 4/2011 |
| WO | 2013008106 A1 | 1/2013 |

OTHER PUBLICATIONS

Notice of Allowance for U.S. Appl. No. 14/175,165 dated May 29, 2014 (28 pages).
European Examination Report for Application No. 10779358.0, dated Feb. 19, 2014 (4 pages).
International Preliminary Report on Patentability dated Oct. 24, 2011 for PCT/US2010/051145 (12 pages).
Non-Final Office Action for U.S. Appl. No. 12/896,578 dated Sep. 19, 2013 (16 pages).
Non-Final Office Action for U.S. Appl. No. 12/896,578 dated Oct. 3, 2012 (16 pages).
Notice of Allowance for U.S. Appl. No. 12/896,593 dated Nov. 7, 2013 (13 pages).
Notice of Allowance for U.S. Appl. No. 12/896,593 dated Aug. 15, 2013 (11 pages).
Advisory Action for U.S. Appl. No. 12/896,593 dated Apr. 10, 2013 (7 pages).
Final Office Action for U.S. Appl. No. 12/896,593, dated Jan. 3, 2013 (13 pages).
Non-Final Office Action for U.S. Appl. No. 12/896,593 dated Sep. 5, 2012 (17 pages).
Electric Motion Company, webpage "Telephony & CATV Products [Bronze Vise Type Connectors]" published Aug. 19, 2007, retrieved via Wayback Machine Jun. 20, 2016 (11 pages).
Southern Grounding Products, webpage "Grounding & ground Rod Clamps" published Nov. 19, 2008, retrieved via Wayback Machine Jun. 20, 2016 (5 pages).
Final Office Action for U.S. Appl. No. 13/343,283 dated Jul. 15, 2016 (22 pages).
Non-Final Office Action for U.S. Appl. No. 13/343,283, dated Jan. 13, 2016 (19 pages).
Non-Final Office Action for U.S. Appl. No. 14/175,165 dated Jan. 5, 2016 (22 pages).
Advisory Action for U.S. Appl. No. 14/175,165, dated Sep. 25, 2015 (6 pages).
Advisory Action for U.S. Appl. No. 13/343,283, dated Aug. 28, 2015 (4 pages).
Final Office Action for U.S. Appl. No. 14/175,165, dated Jun. 12, 2015 (16 pages).
Final Office Action for U.S. Appl. No. 13/343,283, dated May 26, 2015 (18 pages).
Non-Final Office Action for U.S. Appl. No. 14/175,165, dated Mar. 3, 2015 (12 pages).
Final Office Action for U.S. Appl. No. 14/175,165, dated Dec. 4, 2014 (13 pages).
Extended European Search Report for Serial No. 14182496.1, dated Nov. 28, 2014 (7 pages).
Non-Final Office Action for U.S. Appl. No. 13/343,283, dated Oct. 2, 2014 (26 pages).
Non-Final Office Action for U.S. Appl. No. 14/175,165, dated Aug. 15, 2014 (17 pages).
Australian Examination Report for Application No. 2010300379, dated May 30, 2014 (4 pages).
PCT Search Report dated Apr. 28, 2011 for PCT/US2010/051132 (17 pages).
Jasper R. Daube et al., Clinical Neurophysiology, Third Edition, Oxford University Press. Chapters 25, 43 and 44, @ 2009 (71 pages).
PCT Search Report dated Feb. 4, 2011 for PCT/US2010/051145 (15 pages).
International Preliminary Report on Patentability for PCT/US2010/051132, dated Dec. 5, 2011 (5 pages).
"Applications of High-Pressure Balloons in the Medical Device Industry", 1999 Advanced Polymers, Inc. 1999, Mark A. Saab, President (19 pages).
International Search Report and Written Opinion, PCT/US2014/027810, dated Jul. 25, 2014 (18 pages).
International Search Report and Written Opinion, PCT/US2013/072193, dated Mar. 11, 2014 (18 pages).
U.S. Appl. No. 61/244,402, filed Sep. 21, 2009 (11 pages).
Defendants' Invalidity Contentions and Document Production Pursuant to Patent Local Rules 3-3 and 3-4; Neurovision Medical Products, Inc. v. Medtronic Public Limited Company, Medtronic, Inc.; Medtronic Xomed, Inc. HCA Holdings, Inc.; and Healthtrust Purchasing Group, L.P.; Civ. No. 2:16-cv-00127-JRP-RSP, signed by James M. Hilmert, date Jun. 10, 2016 (147 pages).
Hon, Li & Hutchings, "Direct writing technology—Advances and developments," CIRP Annals—Manufacturing Technology, vol. 57, Issue 2, presented on Aug. 25, 2008 and published Oct. 28, 2008, pp. 601-620 (20 pages).
Kartush et al., "Intraoperative Facial Nerve Monitoring," Ch. 5, Neuromonitoring in Otology and Head and Neck Surgery, Raven Press, Ltd., p. 99-120 (1992) (22 pages).
Goldstone A., Schettino R., "The Electrode Endotracheal Tube: A State of the Art Method for Monitoring the Recurrent Laryngeal Nerve-Vocal Cord Muscle Integrity in the Intubated Patient," presented to the American Academy of Otolaryngology/Head & Neck Surgery Annual National Meeting, San Diego, CA. (Sep. 1990) (1 page).

(56) References Cited

OTHER PUBLICATIONS

Eisele D.W. Goldstone A., "Electrophysiologic Identification and Preservation of the Superior Laryngeal Nerve During Thyroid Surgery," The Laryngescope, vol. 101, Issue 3, pp. 313-315 (Mar. 1991) (3 pages).
Bakhshaee et al., "Evaluation of the Distance Between Anterior Commissure of True Vocal Folds and the First Tracheal Ring and Related Laryngeal Indices in 40 Human Cadavers," J. Voice, vol. 30, No. 2, p. 159, col. 1 (2016) (3 pages).
Sprinzl et al., "Morphometric Measurements of the Cartilaginous Larynx: an Anatomic Correlate of Laryngeal Surgery," Head & Neck, Figs. 3-4, Tables 2-3, p. 743-750 (Dec. 1999) (8 pages).
Will, Robert L., "Recurrent Laryngeal Nerve Electrophysiologic Monitoring in Thyroid Surgery: The Standard of Care?" J. Voice, vol. 19, No. 3, pp. 497-500 (2005) (4 pages).
Strauss, Christian et al., "Electrophysiological Localization of Motor Areas within the Rhomboid Fossa During Brainstem Surgery," ECoG, OAE and Intraoperative Monitoring: Proceedings of the First International Conference, (D. Höhmann, ed.) pp. 375-378 (Sep. 1992) (10 pages).
Møller, Aage R., "Monitoring and Mapping the Cranial Nerves and the Brainstem," Ch. 13, Neurophysiology in Neurosurgery: A Modern Intraoperative Approach, Academic Press, pp. 291-318 (2002) (36 pages).
Wang et al., "Prognostic Indicators of Unilateral Vocal Fold Paralysis," Archives of Otolaryngology Head Neck Surgery, vol. 134, No. 4, pp. 380-388 (Apr. 2008) (11 pages).
Dimopoulos et al., "Quantitative Estimation of the Recurrent Laryngeal Nerve Irritation by Employing Spontaneous Intraoperative Electromyographic Monitoring During Anterior Cervical Discectomy and Fusion," J. Spinal Disorder Tech, vol. 22, No. 1, pp. 1-7 (Feb. 2009) (7 pages).
Ajmani, M. L., "A Metrical Study of the Laryngeal Skeleton in Adult Nigerians," J. Anal, vol. 171, pp. 187-191 (1990) ("Ajmani Article") (5 pages).
Grillo, Hermes, Surgery of the Trachea and Bronchi, BC Decker Inc., pp. 39-59 (2004) (23 pages).
Livingstone, Churchill, Gray's Anatomy, pp. 1637-1657 (1995) (28 pages).
Special 510(k) Premarket Notification, K094054, Neurovision® EMG Endotracheal Tube dated May 14, 2010 (6 pages).
Pictures of a NuVasive Emg tube (5 pages). The first public use of the NuVasive EMG tube is unclear to Applicant. For purposes of Examination only, the NuVasive EMG tube may be considered to be prior art to the present application, although Applicant reserves the right to challenge this in any future proceeding. Applicant also intends to submit a physical sample of the NuVasive EMG tube in U.S. Appl. No. 15/217,572, filed Jul. 22, 2016.
U.S. Appl. No. 13/688,818, Notice of Allowance dated Feb. 20, 2015 (7 pages).
U.S. Appl. No. 13/688,818, Final Office Action dated Jun. 25, 2014 (10 pages).
U.S. Appl. No. 13/688,818, Non-Final Office Action dated Mar. 13, 2014 (10 pages).
U.S. Appl. No. 14/747,257, Non-Final Office Action dated Nov. 17, 2015 (10 pages).
U.S. Appl. No. 14/747,257, Notice of Allowance dated Mar. 23, 2016 (5 pages).
U.S. Appl. No. 13/826,323, Examiner's Answer dated Nov. 18, 2015 (6 pages).
U.S. Appl. No. 13/826,323, Advisory Action dated May 28, 2015 (3 pages).
U.S. Appl. No. 13/826,323, Final Office Action dated Mar. 23, 2015 (6 pages).
U.S. Appl. No. 13/826,323, Non-Final Office Action dated Dec. 15, 2014 (11 pages).
U.S. Appl. No. 13/826,323, Non-Final Office Action dated Sep. 8, 2014 (9 pages).
David L. Bourell et al., Solid Freeform Fabrication Proceedings, Aug. 2004, © 2004 The University of Texas at Austin (15 pages).
ECOM™ Brochure for Endotracheal Cardiac Output Monitor, © 2008 ConMed Corporation Sep. 2008 (2 pages).
James K. Brown et al., Parasympathetic Innervation of the Cervical Trachealis Muscle in Living Dogs, © 1982 The American Physiology Society, vol. 53, No. 3, pp. 617-625 (9 pages).
NuVasive® NVJJB® EMG Endotracheal Tube IFU Product Insert (2 pages). We are not certain of its date, but for purposes of examination we request the examiner consider it as possible art. Applicant expressly reserves the right to contest the prior art date of this document should the Examiner find it relevant.
NuVasive® NeuroVision® EMG Endotracheal Tube brochure—© 2010 NuVasive, Inc. (4 pages).
Cahide Topsakal et al., Intraoperative Monitoring of Lower Cranial Nerves in Skull Base Surgery: Technical Report and Review of 123 Monitored Cases, Neurosurg. Rev., vol. 31, pp. 45-52 Published Online Oct. 24, 2007 © Springer-Verlag 2007 (9 pages).
U.S. Appl. No. 15/217,572, filed Jul. 22, 2016, Inventor: David C. Hacker (65 pages).
U.S. Appl. No. 14/716,351, Non-Final Office Action dated Sep. 21, 2016 (6 pages).
Notice of Allowance for U.S. Appl. No. 14/175,165 dated Feb. 23, 2017 (13 pages).
Restriction Requirement for U.S. Appl. No. 12/896,578 dated Jul. 24, 2012 (8 pages).
Notice of Allowance for U.S. Appl. No. 12/896,578 dated Feb. 27, 2014 (7 pages).
Notice of Allowance for U.S. Appl. No. 12/896,578 dated Jun. 9, 2014 (11 pages).
Notice of Allowance for U.S. Appl. No. 12/896,578 dated Aug. 5, 2014 (12 pages).
Notice of Allowance for U.S. Appl. No. 12/896,578 dated Oct. 6, 2014 (11 pages).
Notice of Allowance for U.S. Appl. No. 12/896,578 dated Jan. 28, 2015 (12 pages).
Notice of Allowance for U.S. Appl. No. 12/896,578 dated Mar. 30, 2015 (11 pages).
Canadian 1st Examiner's Report for 2775588 dated Oct. 28, 2016 (4 pages).
Chinese 1st Office Action for 201080054559.2 dated Feb. 14, 2014 (5 pages).
Chinese 2nd Office Action for Application No. 201080054559.2, dated Jul. 17, 2014 (10 pages).
Japanese Office Action for Application No. 2012/532,355, dated Apr. 18, 2014 (7 pages).
European Examination Report for Application No. 10781544.1, dated Feb. 19, 2014 (4 pages).
Restriction Requirement for U.S. Appl. No. 14/716,351 dated Jan. 22, 2016 (5 pages).
Non-Final Office Action for U.S. Appl. No. 14/716,351 dated May 3, 2016 (25 pages).
Australian Examination Report No. 1 for Application No. 2015200049, dated Mar. 10, 2016 (3 pages).
Canadian 1st Examiner's Report for 2776163 dated Oct. 28, 2016 (4 pages).
Chinese 1st Office Action for 201080054850.X dated Feb. 20, 2014 (19 pages).
Chinese 2nd Office Action for Application No. 201080054850.X, dated Jul. 23, 2014 (6 pages).
Extended European Search Report for Application No. 16176750.4, dated Nov. 22, 2016 (6 pages).
Japanese Office Action for Application No. 2012/532,356, dated Apr. 18, 2014 (7 pages).
Japanese Office Action for Application No. 2014/189873, dated Aug. 30, 2015 (5 pages).
Final Office Action for U.S. Appl. No. 14/175,165 dated May 19, 2016 (24 pages).
Advisory Action for U.S. Appl. No. 13/343,283 dated Sep. 26, 2016 (4 pages).
Australian 1st Examination Report for 2012363699 dated Sep. 8, 2016 (3 pages).
Chinese 1st Office Action for 201280071074.3 dated Oct. 30, 2015 (12 pages).

(56) References Cited

OTHER PUBLICATIONS

Japanese 1st Office Action for 2014-551252 dated Oct. 20, 2016 (3 pages).
Non-Final Office Action for U.S. Appl. No. 13/688,818 dated Oct. 9, 2014 (7 pages).
Australian 1st Examination Report for 2013406220 dated May 19, 2016 (3 pages).
European Office Action for Application No. 14720826.8, dated Aug. 2, 2016 (8 pgs).
U.S. Appl. No. 14/945,167, filed Nov. 18, 2015 (89 pages).
U.S. Appl. No. 14/945,208, filed Nov. 18, 2015 (88 pages).
Final Office Action for U.S. Appl. No. 13/343,283 dated Jan. 6, 2017 (24 pages).
Affidavit of Christopher Butler with Exhibit A dated Nov. 10, 2016 (8 pages).
Decision-Institution of Inter Partes Review; *Medtronic Xomed, Inc.* v. *Neurovision Medical Products, Inc.*; PTAB Case IPR2016-01405; for U.S. Pat. No. 8,634,894 entered Dec. 29, 2016 (35 pages).
Petition for Inter Partes Review; *Medtronic Xomed, Inc.* v. *Neurovision Medical Products, Inc.*; PTAB Case IPR2016-01405; for U.S. Pat. No. 8,634,894 dated Dec. 9, 2016 (58 pages).
Patentee's Preliminary Response to Petition for Inter Partes Review; *Medtronic Xomed, Inc.* v. *Neurovision Medical Products, Inc.*; PTAB Case IPR2016-01405; for U.S. Pat. No. 8,634,894 dated Oct. 20, 2016 (74 pages).
Declaration of Mike Lieu—Exhibit 2002 to Patentee's Preliminary Response to Petition for Inter Partes Review dated Oct. 20, 2016 (7 pages).
Declaration of Stephen W. Blakely—Exhibit 2003 to Patentee's Preliminary Response to Petition for Inter Partes Review dated Oct. 20, 2016 (7 pages).
Declaration of James Lee Rea—Exhibit 2004 to Patentee's Preliminary Response to Petition for Inter Partes Review dated Oct. 20, 2016 (6 pages).
Declaration of Ryan M. Rea—Exhibit 2005 to Patentee's Preliminary Response to Petition for Inter Partes Review dated Oct. 20, 2016 (2 pages).
"Thyroid Surgery May Result in Paralysis of Vocal Cords," Wall Street Journal article dated Aug. 10, 2001 to Exhibit 2006 to Patentee's Preliminary Response to Petition for Inter Partes Review dated Oct. 20, 2016 (4 pages).
Medtronic webpage at http://medtronic.com/us-enThealthcare-nim-nerve-monitoring-systems/related-nerve-monitoring-products.html—Exhibit 2007 to Patentee's Preliminary Response to Petition for Inter Partes Review dated Oct. 20, 2016 (5 pages).
Medtronic product recall notice—Exhibit 2008 to Patentee's Preliminary Response to Petition for Inter Partes Review dated Oct. 20, 2016 (4 pages).
MicroPenning: How It Works—Exhibit 2009 to Patentee's Preliminary Response to Petition for Inter Partes Review dated Oct. 20, 2016 (2 pages).
VlicroPenning: Overview—Exhibit 2010 to Patentee's Preliminary Response to Petition for Inter Partes Review dated Oct. 20, 2016 (3 pages).
U.S. Pat. No. 4,461,304 to Kuperstein—Exhibit 2011 to Patentee's Preliminary Response to Petition for Inter Partes Review dated Oct. 20, 2016 (10 pages).
U.S. Appl. No. 61/126,567—Exhibit 2012 to Patentee's Preliminary Response to Petition for Inter Partes Review dated Oct. 20, 2016 (8 pages).
NuVasive, Inc.'s Petition for Inter Partes Review file in IPR2015-00502—Exhibit 2014 to Patentee's Preliminary Response to Petition for Inter Partes Review dated Oct. 20, 2016 (63 pages).

PTAB's Decision dated Jul. 16, 2015 in IPR2015-00502—Exhibit 2015 to Patentee's Preliminary Response to Petition or Inter Partes Review dated Oct. 20, 2016 (31 pages).
Table of page cites and summary regarding Exhibit 2001—Exhibit 2016 to Patentee's Preliminary Response to Petition or Inter Partes Review dated Oct. 20, 2016 (14 pages).
Redacted Exhibit 2001—Confidential Neurovision emails regarding conception and reduction to practice—Exhibit 2017 to Patentee's Preliminary Response to Petition for Inter Partes Review dated Oct. 20, 2016 (140 pages).
Non-Final Office Action for U.S. Appl. No. 15/217,572 dated Feb. 9, 2017 (13 pages).
Korean 1st Office Action for 10-2012-7011251 dated Feb. 6, 2017 (13 pages).
Final Office Action for U.S. Appl. No. 14/716,351 dated Mar. 21, 2017 (30 pages).
Corrected Notice of Allowability for U.S. Appl. No. 14/175,165 dated Mar. 23, 2017 (18 pages).
Decision; *Medtronic Xomed, Inc.* v. *Neurovision Medical Products, Inc.*; PTAB Case IPR2016-01847; for U.S. Pat. No. 8,467,844 entered Mar. 23, 2017 (37 pages).
Non-Final Office Action for U.S. Appl. No. 14/716,351 dated May 17, 2017 (13 pages).
Notice of Allowance for U.S. Appl. No. 14/175,165 dated May 22, 2017 (12 pages).
Final Office Action for U.S. Appl. No. 15/217,572 dated Jun. 6, 2017 (22 pages).
Notice of Allowance for U.S. Appl. No. 13/826,323 dated Jun. 7, 2017 (5 pages).
European Office Action for Application No. 14720826.8, dated Feb. 1, 2017 (6 pages).
Australian 2nd Examination Report for 2012363699 dated Jun. 22, 2017 (6 pages).
Canadian 2nd Examiner's Report for 2775588 dated Sep. 5, 2017 (4 pages).
Korean Final Office Action for 10-2012-7011251 dated Jun. 28, 2017 (7 pages).
Notice of Allowance for U.S. Appl. No. 14/716,351 dated Sep. 27, 2017 (11 pages).
Advisory Action for U.S. Appl. No. 15/217,572 dated Sep. 29, 2017 (4 pages).
Notice of Allowance for U.S. Appl. No. 15/217,572 dated Nov. 3, 2017 (10 pages).
Final Office Action for U.S. Appl. No. 13/343,283 dated Jul. 11, 2017 (28 pages).
Notice of Allowance for U.S. Appl. No. 13/343,283 dated Oct. 12, 2017 (12 pages).
Corrected Notice of Allowability for U.S. Appl. No. 13/343,283 dated Nov. 1, 2017 (15 pages).
Australian 3rd Examination Report for 2012363699 dated Sep. 5, 2017 (3 pages). (.141).
European Office Action for Application No. 13812262.7, dated Aug. 2, 2017 (8 pages).
Notice of Allowance for U.S. Appl. No. 13/826,323 dated Sep. 12, 2017 (45 pages).
Australian 1st Examination Report for Application No. 2014236572, dated Aug. 10, 2017 (4 pgs).
Japanese 1st Office Action for 2016-502632 dated Jul. 7, 2017 (5 pages).
European Office Action for Application No. 14720826.8, dated Jul. 17, 2017 (6 pgs).
International Search Report and Written Opinion, PCT/US2012/069253, dated Feb. 28, 2013 (4 pages).
European Examination Report for Application No. 12818693.9 dated Oct. 25, 2017 (7 pages).

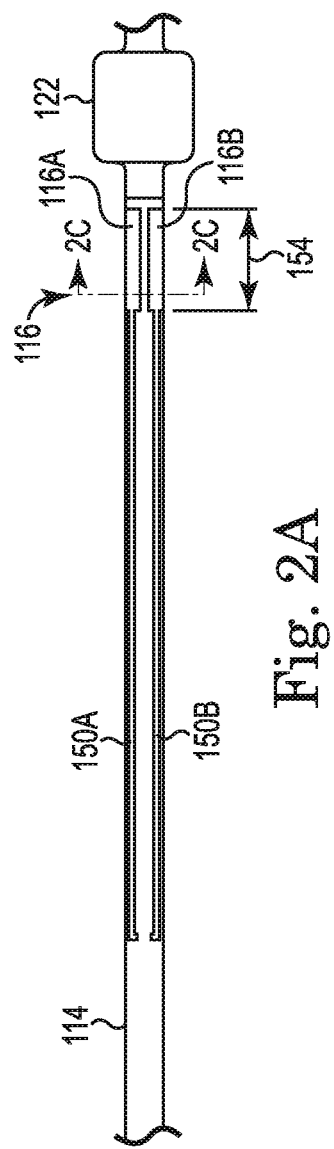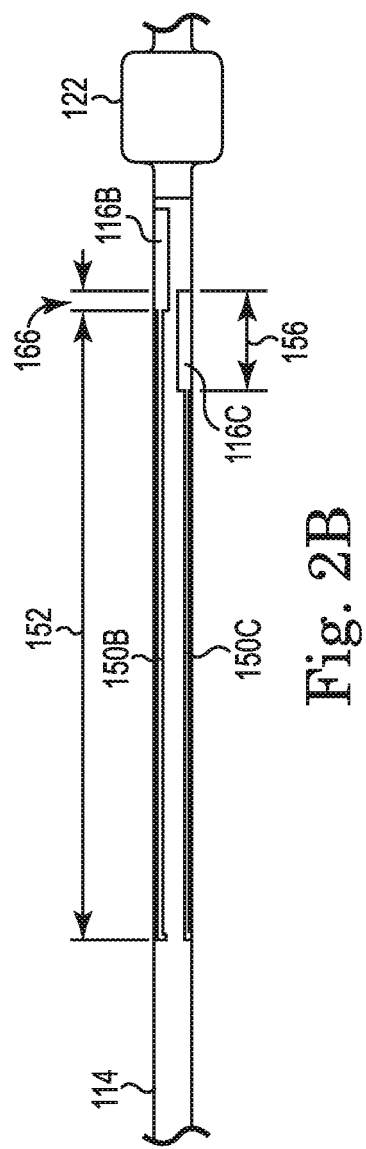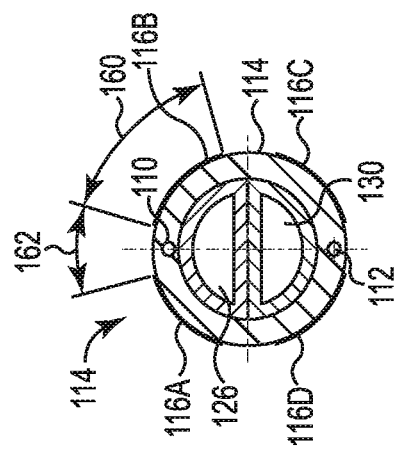

ENDOBRONCHIAL TUBE APPARATUS

CROSS-REFERENCE TO RELATED APPLICATIONS

This application is a continuation of U.S. application Ser. No. 14/747,257, filed Jun. 23, 2015, now U.S. Pat. No. 9,398,865, which is a continuation of U.S. application Ser. No. 13/688,818, filed Nov. 29, 2012, now U.S. Pat. No. 9,060,744, the specifications of which are incorporated by reference herein.

BACKGROUND

Endobronchial tubes (also known as dual-lumen endotracheal tubes) provide an open airway for patient ventilation during surgery. In particular, endobronchial tubes are used during surgical procedures to provide ventilation to individual lungs separately. Current endobronchial tubes include a first, tracheal lumen and a second, bronchial lumen. Each lumen includes an associated inflatable cuff, the cuff associated with the tracheal lumen being positioned within the trachea and the cuff associated with the bronchial lumen being positioned within one of the bronchus.

SUMMARY

Concepts presented herein include an apparatus for monitoring EMG signals of a patient's laryngeal muscles. The apparatus includes an endobronchial tube having an exterior surface and two lumens for providing ventilation. Conductive ink electrodes are formed on the exterior surface of the endobronchial tube. The conductive ink electrodes are configured to receive the EMG signals from the laryngeal muscles when the endotracheal tube is placed in a trachea of the patient. At least one conductor is coupled to the conductive ink electrodes and is configured to carry the EMG signals received by the conductive ink electrodes to a processing apparatus.

BRIEF DESCRIPTION OF THE DRAWINGS

FIGS. 2A and 2B are different side views of an endobronchial tube.

FIG. 2C is a sectional view of the endobronchial tube illustrated in FIG. 2A.

DETAILED DESCRIPTION

Figure 1:
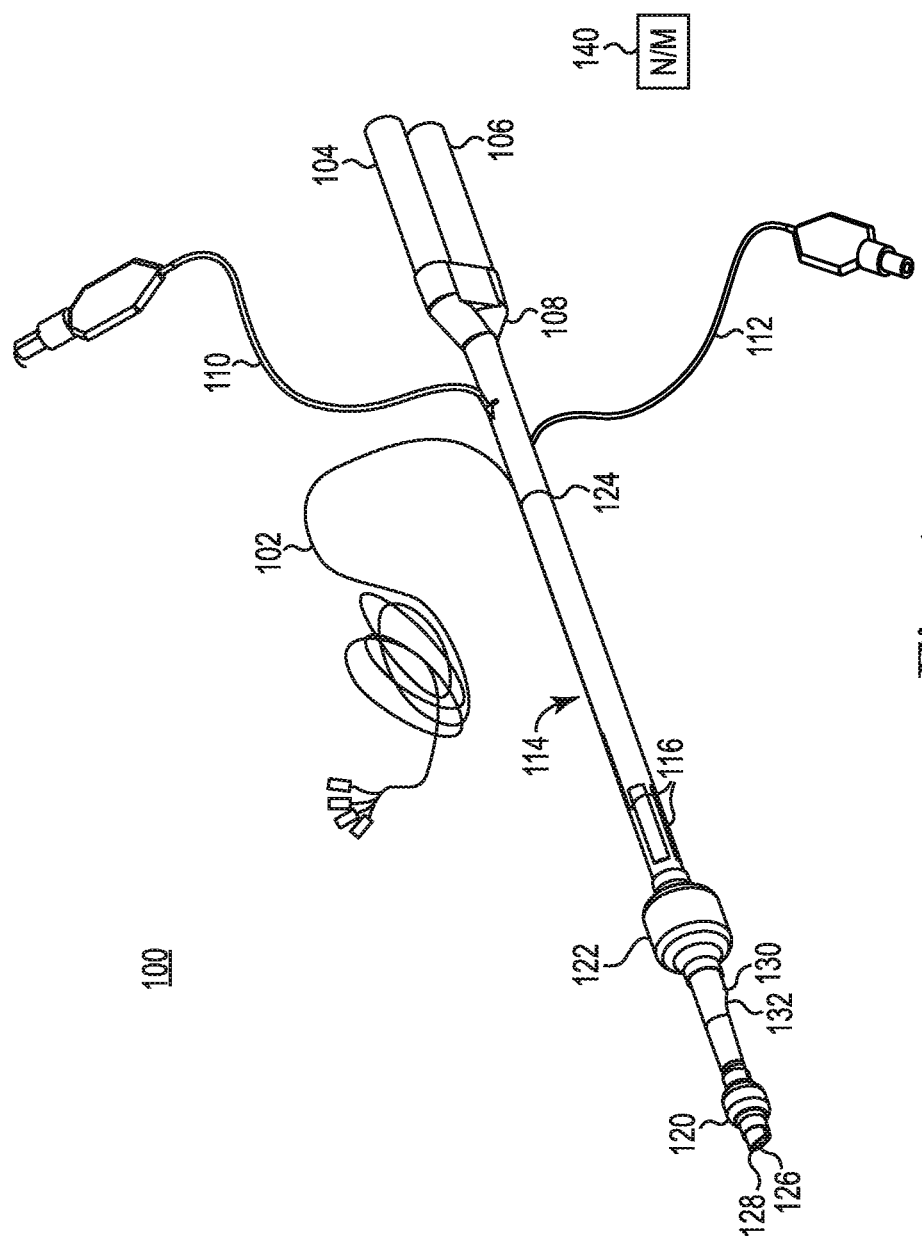
FIG. 1 is a schematic view of an EMG endobronchial tube.

FIG. 1 shows an EMG endobronchial tube 100 made from extruded polymer. Endobronchial tube 100 includes solid wires 102, a bronchial fitting 104, a tracheal fitting 106, a y-connector 108, a bronchial cuff inflating conduit 110, a tracheal cuff inflating conduit 112, extruded polymer tube 114, electrodes 116, bronchial cuff 120 and tracheal cuff 122. Solid wires 102 are connected to electrodes 116 at an interconnection 124. Tube 114 transports gases to and from the lungs. In particular, tube 114 defines a first, bronchial lumen 126 extending from bronchial fitting 104 to an opening 128 distal the bronchial cuff 120 and a second, tracheal lumen 130 extending from tracheal fitting 106 to an opening 132 distal the tracheal cuff 122. The Y-connector 108 fluidly couples the bronchial fitting 104 and tracheal fitting 106 to bronchial lumen 126 and tracheal lumen 130, respectively.

Fittings 104 and 106 are configured to be connected to a respirating machine (not shown) for injecting air into the lungs and withdrawing air from the lungs. Cuff inflating conduits 110 and 112 are configured to be connected to a source of compressed air (not shown) for inflating cuffs 120 and 122. Cuff inflating conduit 110 communicates with a lumen located in the wall of tube 114, and the lumen communicates with bronchial cuff 120. Likewise, tracheal cuff inflating conduit 112 communicates within a lumen located in the wall of tube 114, and the lumen communicates with tracheal cuff 122. During use, one of the fittings (e.g., bronchial fitting 104) is configured to inject air into one lung while the other fitting (e.g., tracheal fitting 106) is configured to injected air into the other lung. For example, cuff 120 can be positioned into the left bronchus and cuff 122 positioned into the trachea. In this case, opening 126 is positioned to direct air into the left lung from bronchial fitting 104 while opening 132 is positioned to direct air into the right lung from tracheal fitting 106. Selectively, air can be provided to only one of the fittings 104, 106 so as to provide air to only a single lung and collapsing the other lung. In such a case, a surgeon can operate proximate the collapsed lung or on the collapsed lung. After endobronchial tube 100 is inserted into the trachea of a patient, electrodes 116 sense EMG signals, which are output to an EMG processing machine, such as nerve integrity monitor (NIM) device 140, via solid wires 102. Die cut tape may be used to tape tube 114 to a patient's mouth to secure the tube and keep it appropriately positioned.

In one embodiment, the NIM 140 is configured to determine when the electrodes 116 are in contact with the vocal folds, and is configured to provide an alert to the surgeon when such contact is lost. In one embodiment, the NIM 140 is also configured to determine whether the electrodes 116 are in contact with muscle or tissue based on the received signals In one embodiment, tube 114 is a braided tube that is more flexible than conventional solid polymer tubes, and that reduces kinking. Tube 114 according to one embodiment is formed from a braided polymer or nitinol within a thin-walled tube, and reduces or eliminates rotation of the tube at the vocal folds, while allowing a proximal portion of the tube to rotate.

FIG. 2A shows a first side view (posterior side) of endobronchial tube 114 with four electrodes 116. FIG. 2B shows a second side view (rotated 90 degrees from the view shown in FIG. 2A) of the endobronchial tube 114 shown in FIG. 2A. FIG. 2C is a diagram illustrating a cross-sectional view of the endobronchial tube 114 shown in FIGS. 2A and 2B.

Electrodes 116 include four electrodes 116A-116D, which are formed around a circumference of the tube 114 and extend in a longitudinal direction of the tube 114. Electrodes 116A and 116B are positioned entirely on the posterior side of the tube 114 and are also referred to herein as posterior electrodes 116A and 116B. Electrodes 116C and 116D are positioned entirely on the anterior side of the tube 114 and are also referred to as anterior electrodes 116C and 116D. The anterior side of the tube 114 is the bottom half of the tube 114 shown in FIG. 2C, and the posterior side of the tube 114 is the top half of the tube 114 shown in FIG. 2C. Each of the electrodes 116A-116D is coupled to a respective trace 150A-150D (trace 150D is not visible in the Figures). Traces 150A-150D are positioned in a protected (masked) region 152 of tube 114. Posterior electrodes 116A and 116B are positioned in an exposed (unmasked) region 154 of tube 114. Anterior electrodes 116C and 116D are positioned in an exposed (unmasked) region 156 of tube 114.

In one embodiment, each of the electrodes 116A-116D has a length of about one inch, and extends laterally around a circumference of the tube for a distance corresponding to an angle 160 of about 60 degrees (i.e., each of the electrodes 116A-116D has a width of about 16.67 percent of the total circumference of the tube). The electrodes are laterally spaced apart around the circumference of the tube by a distance corresponding to an angle 160 of about 30 degrees (i.e., the lateral spacing between each of the electrodes 116A-116D is about 8.333 percent of the total circumference of the tube). The posterior electrodes 116A and 116B are longitudinally offset or displaced from the anterior electrodes 116C and 116D. The posterior electrodes 116A and 116B are positioned closer to the distal end (right side in FIGS. 2A and 2B) of the tube 114 than the anterior electrodes 116C and 116D, and the anterior electrodes 116C and 116D are positioned closer to the proximal end (left side in FIGS. 2A and 2B) of the tube 114 than the posterior electrodes 116A and 116B.

Tube 114 includes an overlap region 166 where a proximal portion of the posterior electrodes 116A and 116B longitudinally overlap with a distal portion of the anterior electrodes 116C and 116D. The electrodes 116 do not physically overlap each other since they are laterally offset from each other. In one embodiment, the overlap region 166 is about 0.1 inches long, and the overall length from a proximal end of the anterior electrodes 116C and 116D to a distal end of the posterior electrodes 116A and 116B is about 1.9 inches. In another embodiment, the overlap region 166 is about 0.2 inches long, and the overall length from a proximal end of the anterior electrodes 116C and 116D to a distal end of the posterior electrodes 116A and 116B is about 1.8 inches. Tube 114 is configured to be positioned such that the vocal folds of a patient are positioned in the overlap region 166. Thus, the configuration of the electrodes 116 above the vocal folds is different than the configuration below the vocal folds. The posterior electrodes 116A and 116B are configured to be positioned primarily below the vocal folds, and the anterior electrodes 116C and 116D are configured to be positioned primarily above the vocal folds. In one embodiment, electrodes 116A and 116C are used for a first EMG channel, and electrodes 116B and 116D are used for a second EMG channel.

In an alternate embodiment, all four surface printed electrodes, 116A, 116B, 116C and 116D, are equal in length. This will allow the finish product to be placed with little concerns of rotational alignment.

As illustrated in FIG. 2C, conduits 110 and 112 are formed in a thickness of the tube 114 to carry compressed air to bronchial cuff 120 and tracheal cuff 122, respectively. Additionally, inside tube 114 are formed bronchial lumen 126 and tracheal lumen 130. During use, one of the lumens 126 and 130 can be used to inject gases into a particular lung while the other lumen is sealed from injecting gases into the opposite lung.

Figure 3:
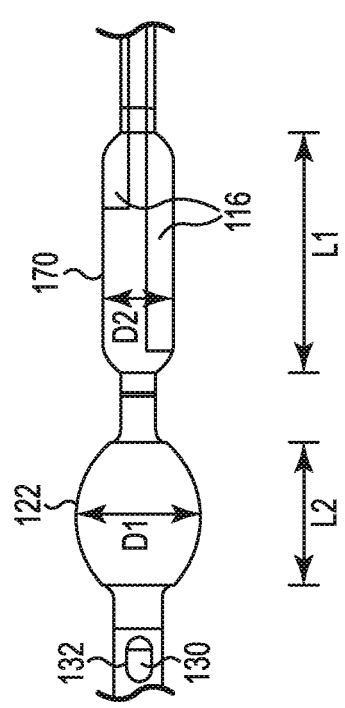
FIG. 3 is a partial side view of an endobronchial tube having an electrode cuff.

With reference to FIG. 3, another embodiment includes an electrode cuff 170 positioned proximal the tracheal cuff 122. In the embodiment of FIG. 3, cuff 122 is of a different shape than that illustrated in FIGS. 1-2C. Other shapes for the cuffs 122 and 170 can be utilized. Electrodes 116 are applied directly to the electrode cuff 170 and are similar to that discussed above. Cuffs 122 and 170 are sized so as to both provide suitable sealing between the trachea and cuff 122 yet provide suitable compliance of electrode cuff 170 in contact with the vocal folds of a patient when inflated by pressurized fluid provided within inflating conduit 110. Upon inflation, the tracheal cuff 122 has a larger diameter D1 than a diameter D2 of electrode cuff 170. In some embodiments, the diameter D2 is selected to be approximately half the diameter D1. In one example, D1 is about 20 millimeters, whereas D2 is about 9 millimeters. In yet a further embodiment, D1 is approximately 27 millimeters, whereas D2 is approximately 14 millimeters. Moreover, a length L1 of the cuff 170 is selected to be greater than a length L2 for cuff 122. In one embodiment, the L1 is approximately 1.875 inches. In another embodiment, L1 is in a range from approximately 1.5 inches to 2.5 inches. In a further embodiment, a ratio of D1:L1 is selected to be in a range from approximately 15:100 to 30:100.

Furthermore, a compliance for cuff 170 is selected so as to prevent trauma due to cuff 170 contacting the vocal folds of the patient. In one embodiment, the cuff 170 is formed of a semi-compliant balloon. The semi-compliant balloon will increase in diameter about 10 to 20 percent from a nominal pressure to a rated burst pressure for the balloon. In a further embodiment, cuff 170 is formed of a compliant balloon such that the balloon will increase in diameter from 20 to 200 percent from a nominal pressure to a rated burst pressure of the balloon. In a further embodiment, the cuff 170 is formed of a compliant material that has a greater compliance than a material selected for cuff 122. In one embodiment, cuff 122 has a compliance defined as increasing in diameter about 20 to 200 percent from a nominal pressure to a rated burst pressure for the cuff 122.

Inflating conduit 110 extends along the length of tube 114 to electrode cuff 170 and continues in extension to the tracheal cuff 122. Due to relative compliance of the cuffs 122 and 170, cuff 122 is configured to fluidly seal the trachea of a patient when positioned, whereas electrode cuff 170 inflates to contact the vocal folds of the patient so as to prevent trauma from occurring due to contact between the cuff 170 and the vocal folds. Furthermore, by selecting diameters D1 and D2 of cuffs 122 and 170, tension exerted on an exterior surface of each cuff is adjusted. In one embodiment, thickness and diameter for cuffs 122 and 170 are selected such that cuff 122 will absorb pressure and reduce pressure on cuff 170. In this configuration, cuff 170 can conform to a shape of vocal folds and ensure sufficient electrical contact between the electrodes 116 and the vocal folds without causing irritation by exerting too much pressure on the vocal folds.

Although the present disclosure has been described with reference to preferred embodiments, workers skilled in the art will recognize that changes can be made in form and detail without departing from the spirit and scope of the present disclosure.

What is claimed is:
1. An apparatus for monitoring electromyographic signals of a patient's laryngeal muscles, comprising:
  an endobronchial tube defining first and second lumens;
  a first cuff coupled to the endobronchial tube and positioned proximate a first opening fluidly coupled with the first lumen, the first cuff sized to be positioned within a bronchus of the patient;
  a second cuff coupled to the endobronchial tube and positioned proximate a second opening fluidly coupled with the second lumen, the second cuff configured to be positioned within a trachea of the patient; and conductive electrodes exteriorly exposed on a compliant portion positioned on the endobronchial tube that is proximal the first and second cuffs.

2. The apparatus of claim 1, wherein the conductive electrodes include four electrodes positioned around a circumference of the compliant portion.

3. The apparatus of claim 1, further comprising a Y-connector coupled to the endobronchial tube, the Y-connector fluidly coupling first and second fittings to the first and second lumens, respectively.

4. The apparatus of claim 1, further comprising an interconnection coupled to the endobronchial tube and conductive traces electrically connecting the conductive electrodes with the interconnection.

5. The apparatus of claim 1, further comprising first and second inflating conduits fluidly coupled to the first and second cuffs, respectively.

6. The apparatus of claim 5, wherein the compliant portion positioned on the endobronchial tube is fluidly coupled to the second inflating conduit.

7. The apparatus of claim 1, wherein the second cuff is formed of a first material exhibiting a first compliance and wherein the compliant portion positioned on the endobronchial tube is formed of a second material exhibiting a second compliance, greater than the first compliance.

8. The apparatus of claim 1, wherein the conductive electrodes include posterior electrodes and anterior electrodes, wherein the posterior electrodes are positioned closer to a distal end of the endobronchial tube as compared to the anterior electrodes.

9. The apparatus of claim 1, wherein the conductive electrodes are positioned such that, when the first cuff is positioned within the bronchus and the second cuff is positioned within the trachea, the conductive electrodes are in contact with vocal folds of the patient.

10. A method for monitoring electromyographic signals of a patient's laryngeal muscles, comprising:
providing an apparatus including an endobronchial tube defining first and second lumens, the apparatus including conductive electrodes exteriorly exposed on a compliant portion positioned on the endobronchial tube;
positioning a bronchial cuff within a bronchus of the patient, the bronchial cuff being coupled to the endobronchial tube;
positioning a tracheal cuff within a trachea of the patient, the tracheal cuff coupled to the endobronchial tube, wherein the compliant portion positioned on the endobronchial tube is positioned proximal to the bronchial cuff and the tracheal cuff; and
measuring signals of the patient using the conductive electrodes.

11. The method of claim 10, wherein the conductive electrodes include four electrodes positioned around a circumference of the compliant portion positioned on the endobronchial tube.

12. The method of claim 10, further comprising:
coupling a Y connector to the endobronchial tube, the Y connector fluidly coupling first and second fittings to the first and second lumens, respectively.

13. The method of claim 10, further comprising electrically connecting the conductive electrodes to an interconnection on the endobronchial tube with conductive traces.

14. The method of claim 10, further comprising:
inflating the bronchial and tracheal cuffs using first and second inflating conduits, respectively.

15. The method of claim 14, further comprising inflating the compliant portion positioned on the endobronchial tube using the second inflating conduit.

16. The method of claim 10, wherein the tracheal cuff is formed of a first material exhibiting a first compliance and wherein the compliant portion positioned on the endobronchial tube is formed of a second material exhibiting a second compliance, greater than the first compliance.

17. The method of claim 10, wherein the conductive electrodes include posterior electrodes and anterior electrodes, wherein the posterior electrodes are positioned closer to a distal end of the endobronchial tube as compared to the anterior electrodes.

18. The method of claim 10, further comprising:
positioning the conductive electrodes in contact with vocal folds of the patient.

* * * * *